United States Patent [19]

Sibley

[11] 4,396,018

[45] Aug. 2, 1983

[54] APPARATUS AND METHOD FOR DETECTING KOROTKOFF SOUNDS

[76] Inventor: Alfred E. Sibley, 338 Reynolds Dr., Boulder Creek, Calif. 95006

[21] Appl. No.: 244,467

[22] Filed: Mar. 16, 1981

[51] Int. Cl.³ .......................... A61B 7/00; A61B 5/02
[52] U.S. Cl. ..................................... 128/680; 128/773
[58] Field of Search ........ 128/680, 672, 677, 686–687, 128/689, 681–683, 679, 701, 773

[56] References Cited

U.S. PATENT DOCUMENTS

| | | | |
|---|---|---|---|
| 3,101,082 | 8/1963 | Steen et al. | 128/680 |
| 3,334,622 | 8/1967 | Brech | 128/660 |
| 3,581,734 | 6/1971 | Croslin et al. | 128/679 |
| 3,771,515 | 11/1973 | Hurwitz | 128/680 |
| 3,978,848 | 9/1976 | Yen et al. | 128/689 X |
| 4,005,701 | 2/1977 | Aisenberg et al. | 128/680 |
| 4,252,127 | 2/1981 | Gemelke | 128/680 |

FOREIGN PATENT DOCUMENTS

| | | | |
|---|---|---|---|
| 1466809 | 5/1969 | Fed. Rep. of Germany | 128/680 |
| 2555453 | 6/1977 | Fed. Rep. of Germany | 128/680 |

OTHER PUBLICATIONS

Tursky et al., "Automated Constant Coff–Press. System to Measure Avg. Syst. and Diast. BP in Man", *IEEE Trans. on BME;* vol. BME-19, No. 4, 7-1972, pp. 271-276.

Schulze et al., "System for the Auto Measurement and Dig. Display of Syst. and Diast. BP"; SW Inst. of Electrical & Electronics Engr. Conf. Record; 4-1968, pp. 17F1-17F5.

*Primary Examiner*—Lee S. Cohen
*Assistant Examiner*—Angela D. Sykes
*Attorney, Agent, or Firm*—John L. McGannon

[57] ABSTRACT

Apparatus and a method for detecting Korotkoff sounds using a pair of microphones carried by an inflatable cuff adapted to be wrapped around a limb of a patient whose blood pressure is to be determined. A Korotkoff sound is first sensed by one of the microphones to produce a first signal which is coupled to a delay unit which has an output signal delayed by a certain time interval, such as 12 millisecond. At the end of this interval, a window is opened. The same Korotkoff sound is later sensed by the second microphone whose output signal is applied to the window and passes through the window so long as it is open. The output signal then actuates a recorder, such as an oscillograph.

15 Claims, 10 Drawing Figures

APPARATUS AND METHOD FOR DETECTING KOROTKOFF SOUNDS

BACKGROUND OF THE INVENTION

The indirect method of blood pressure determination usually involves the detection of the Korotkoff sounds produced in the vicinity of the brachial artery when a Rive-Rocci cuff is inflated about the arm of a patient to a pressure between the systolic and diastolic values. Numerous studies have been made to identify the origin and nature of these sounds in efforts to improve the accuracy and reliability of the Korotkoff method of measuring blood pressure. Although there is still disagreement as to the exact mechanism by which the sounds are produced, the detection and recording of the sounds is a straightforward process, and the frequency spectrum of the sound energy has been well established by several investigators.

It is with the detection of those sounds in the presence of high noise levels that the present invention is concerned. This task is made particularly difficult because of the resonant nature of the cuff-tissue-arterial system, which tends to produce energy in the band of interest whenever the system is perturbed by noise impulses, either through the limb or via the cuff.

Noise impulses are produced by arm motion, external vibration or motion coupled through the cuff, tubing, or in many cases from the hand up through the tissues, bones, and blood stream to the area beneath the cuff. It appears that the brachial artery itself is a very efficient conductor of such artifacts, and this is an important factor contributing to the difficulty of measuring blood pressures during physical activity, such as an exercise tolerance test.

The fact that externally generated artifacts tend to arrive at all points beneath the cuff within a few milliseconds of each other, regardless of their source or coupling device, makes it possible to identify legitimate Korotkoff sounds by their relatively unique time relationships. Korotkoff sounds never appear within 15 milliseconds of each other at two microphones spaced by 5 cm and located over the brachial artery. Noise impulses are always synchronized within a few milliseconds.

Tests indicate that the events leading to the production of the Korotkoff sound begin with the arrival of the pressure wave at the upper edge of the cuff and are propagated along the brachial artery to the lower edge of the cuff, where the sound is normally detected. The indicated velocity of propagation of this phenomenon approaches the blood flow velocity when the cuff pressure is near systolic value, and approaches the pulse wave velocity when the cuff pressure is near diastolic. Since these two velocities differ by approximately a 10:1 ratio, and artifact sounds or noise impulses tend to travel at the pulse wave velocity or faster, the Korotkoff sounds exhibit unique characteristics when compared to other sound events, and can be discriminated from other sounds even though they may be in the same frequency band.

Furthermore, the determination of diastolic pressure need not depend upon the preception of the "muffling" or "disappearance" of the sound as the cuff is deflated, but can be clearly and specifically identified as the pressure at which the sounds-if any-appear to be propagated at a velocity of 5 meters per second or greater. This represents a delay of less than 10 milliseconds between sounds detected by two microphones spaced 5 cm apart along the artery.

SUMMARY OF THE INVENTION

The present invention provides apparatus and a method for detection of Korotkoff sounds in which each such sound between systolic and diastolic pressure is sensed by a first microphone coupled to a Riva-Rocci cuff and such signal from the first microphone is used, following a time delay such as about 12 milliseconds, to open a window or enable a gate so that when the same sound is sensed by a second microphone spaced from the first microphone, the signal from the second microphone will pass through the gate and provide an output therefore which can be recorded by a suitable output device, such as an oscillograph or the like. In this way, noise or artifacts can be eliminated from the recording of the signals associated with Korotkoff sounds and an accurate measure of blood pressure, using Korotkoff sounds can thereby be obtained.

The primary object of this invention is to provide apparatus and a method for detecting Korotkoff sounds in a manner to eliminate noise and artifacts which heretofore have affected the reliability of the Korotkoff method of measure blood pressure.

Other objects of this invention will become apparent as the following specification progresses, reference being had to the accompanying drawings for an illustration of the invention.

IN THE DRAWINGS

Figure 1:
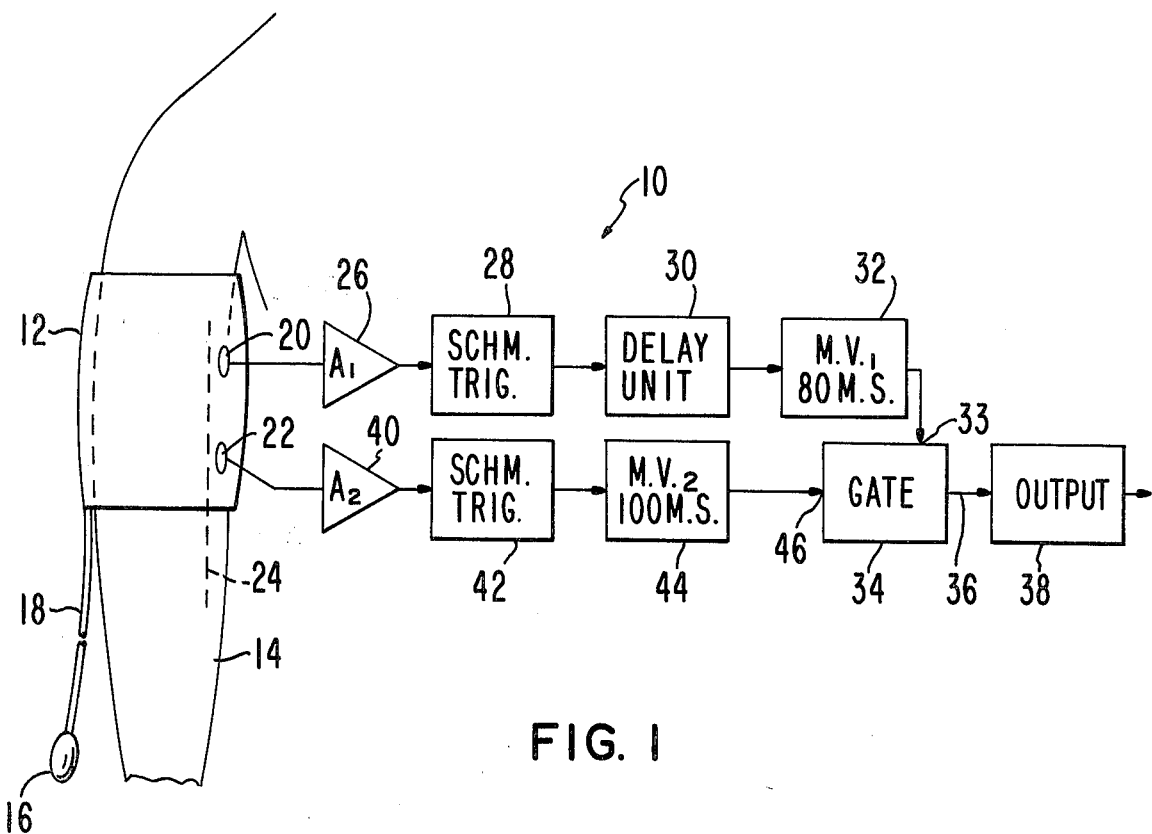
FIG. 1 is a schematic view of the Korotkoff sound detector of the present invention with the cuff of the detector mounted on the arm of a patient whose blood pressure is to be determined.

The apparatus of the present invention is broadly denoted by the numeral 10 and includes a conventional Riva-Rocci cuff 12 capable of being wrapped around the arm 14 of a patient whose blood pressure is to be determined. The cuff is inflatable in a conventional manner by means of a bulb 16 coupled by a tube 18 to the inflatable device in the cuff.

Cuff 12 has a pair of microphones 20 and 22 coupled therewith and spaced apart by a distance of approximately 5 cm. Microphones 20 and 22 are longitudinally aligned with reference to to axis of cuff 12 when the cuff is mounted on arm 14 and the microphones are adapted to overlie the brachial artery 24 in the arm.

The output of microphone 20 is coupled to an amplifier 26, the latter having output coupled to the input of a Schmitt trigger 28. The output of the Schmitt trigger is coupled to a delay circuit 30 whose output is connected to a multivibrator 32 having a duty cycle of about 80 milliseconds. The output of the multivibrator is coupled to an electronic gate 34 of any suitable construction and gate 34 has an output lead 36 coupled to some suitable output device 38, such as an oscillograph or other display device.

The output of microphone 22 is coupled by a lead to a second amplifier 40 and the output signal from this amplifier is coupled to a Schmitt trigger 42. The output of the Schmitt trigger is coupled to a multivibrator 44 having a predetermined duty cycle, such as 100 milliseconds. The output of multivibrator 44 is coupled to the second input 46 of gate 34, the gate, for example, being an and gate which provides an output signal to output device 38 over lead 36 when signals are applied to both gate inputs 33 and 46.

Figure 2:
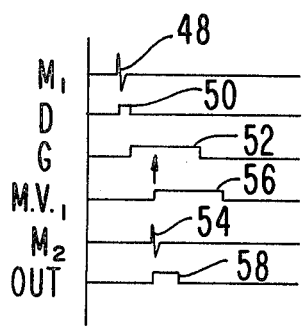
FIG. 2 is a timing diagram showing various signals associated with the apparatus of FIG. 1 for the time when Korotkoff sounds between systolic and diastolic cuff pressures are detected.

FIG. 2 illustrates the operation of apparatus 10. When a first Korotkoff sound is detected by microphone 20 (denoted in FIG. 2 as M1) the signal will be represented by a pulse 48. This signal is amplified by amplifier 26 and the output of the amplifier will eventually reach a threshold detectible by Schmitt trigger 28 which will then have an output to a delay circuit 30, the delay circuit being operable to create a pulse 50 having a duration of about 12 milliseconds. The trailing edge of pulse 50 will actuate multivibrator 32 which will have an output signal applied to input 33 of gate 34. This will enable the gate or open the window represented by the gate, this window being denoted by a pulse 52.

When the same Korotkoff sound is detected by microphone 22, it will generate a pulse 54 which, when applied through amplifier 40 and Schmitt trigger 42, will actuate a multivibrator 44 whose output signal will be represented by pulse 56 having a duration of about 100 milliseconds. This output will be applied to input 46 of gate 34 which will immediately have an output signal applied to the input of output device 38. The output of gate 34 is represented by a pulse 58 in FIG. 2.

In view of the foregoing, it is the Korotkoff sound sensed by microphone 22 which is the true Korotkoff sound free of any artifacts or noise pulses and it is also this sound which is delayed in the above manner which provides a means for opening a window or enabling the gate.

Figure 3:
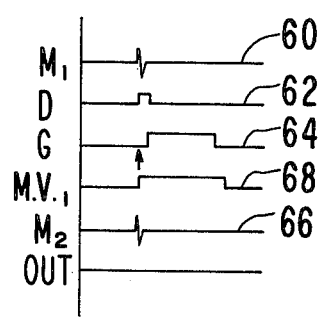
FIG. 3 is a view similar to FIG. 2 but showing the sound below diastolic pressure in the cuff.

A second situation which could arise in the operation of apparatus 10 is a situation in which a sound is sensed below diastolic pressure in cuff 12. The timing diagram associated with this situation is shown in FIG. 3 wherein a pulse 60 sensed by microphone 20 will provide a delay pulse 62 by delay circuit 30, following which multivibrator 32 will apply a pulse 64 to input 33 of gate 34. However, pulse 64 occurs after the noise pulse is sensed by microphone 22 as indicated by pulse 66; thus, while pulse 68 at the output of multivibrator 44 and input 46 of gate 34 is high, it goes high before the gate is opened so that there is no output to device 38.

Figure 4:
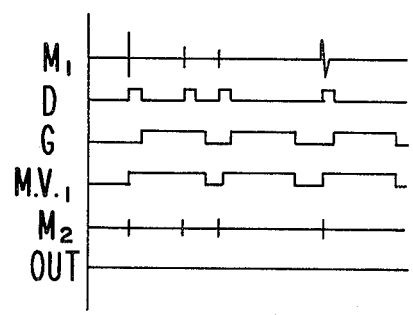
FIG. 4 is view similar to FIGS. 2 and 3 but showing the signals associated with the apparatus of FIG. 1 when miscellaneous noise pulses are detected by the apparatus.

FIG. 4 illustrates the situation where both microphones 20 and 22 detect miscellaneous noise pulses at high density. In each case, the window is not opened following the noise pulse sensed by each microphone 20 because of the delay circuit 30. Thus, the window is not open opened when the noise pulses are sensed by microphone 22. Thus, there is no output signal to device 38 for any of these noise pulses sensed by microphone 22.

Figure 5:
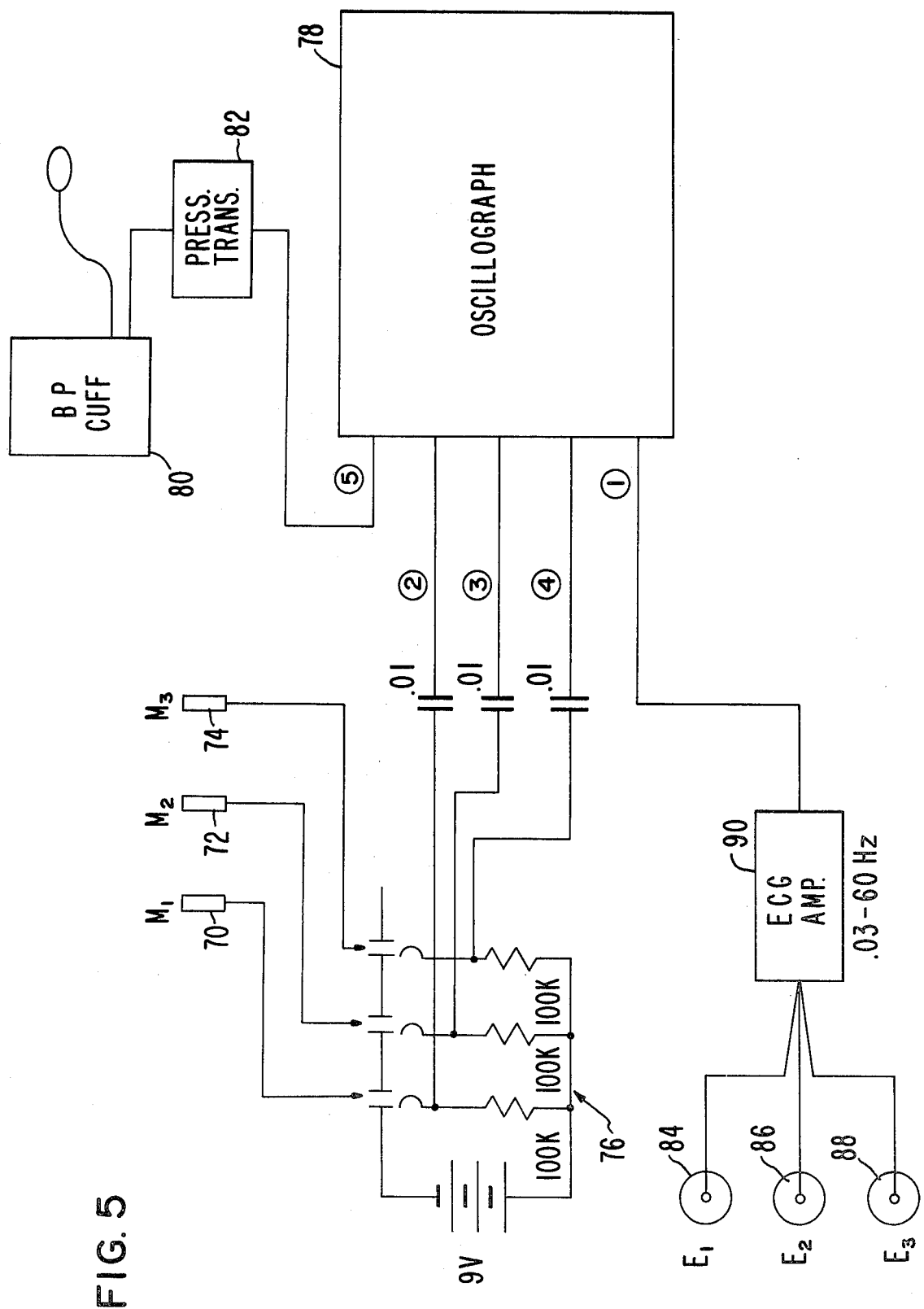
FIG. 5 is a schematic view of apparatus used to conduct pressure tests on a patient at pressures above systolic pressure, at systolic pressure, in the midrange of pressures between systolic and diastolic pressures, at diastolic pressure and below diastolic pressure.
Figure 6:
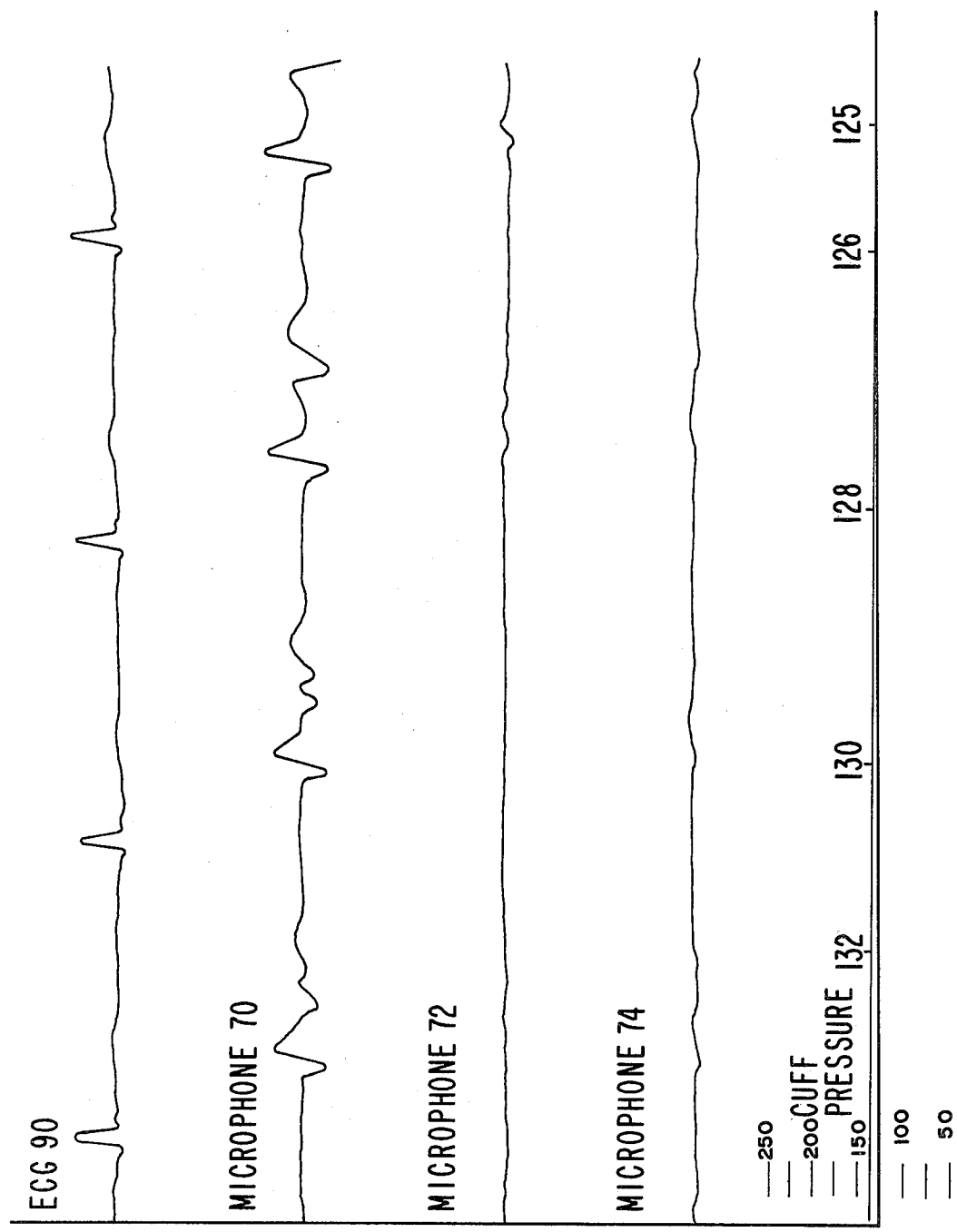
FIGS. 6, 7, 8, 9 and 10 show typical tracings from an oscillograph taken with the cuff inflated to the following pressures: above systolic, at systolic, midrange, at diastolic, and below diastolic.

To show the way in which Korotkoff sounds are sensed by several microphones spaced apart and carried by the cuff, a number of tests were conducted using the system shown in FIG. 5. In this case, three microphones were used with the cuff, the microphones being identical electret units (Knowles BT 1753) housed in chambers with flexible diaphragms, each chamber being 2.3 cm in diameter and 3.5 mm in thickness. The frequency of each microphone fell off at 6 db per octave below 64 Hz, which was the 3 db point. The microphones are denoted by the numerals 70, 72, and 74 in FIG. 5.

The outputs of the microphones are coupled to a power network 76 to the inputs of an oscillograph 78 also having an input coupled to a cuff 80 through a pressure transducer 80. ECG terminals 84, 86 and 88 applied to a patient are coupled through an ECG amplifier 90 to another input of oscillograph 78.

The microphone housings were mounted in a flexible pad having approximately the same thickness as the microphones themselves to minimize the possibility of compressing the arterial wall with the edge of the microphone housing beneath the cuff. This arrangement also assured that the relative spacing of the microphones would be maintained constant in all of the measurements. The three microphones were spaced 5 cm apart and were located by the cuff along the brachial artery, the lowest microphone being just beneath the lower edge of the cuff. This resulted in a symmetrical arrangement of the microphones, with the center unit located at the center of the cuff. The ECG signal was recorded using a modified V-5 electrode placement, and the cuff pressure galvanometer was driven by a Foxboro 49-70 transducer. Recordings were made as the cuff was deflated at a rate of not greater than 3 mm Hg per second from above systolic to below diastolic pressure.

FIGS. 6, 7, 8, 9, and 10 show typical tracings taken with the cuff inflated to above systolic, at systolic, mid-range, at diastolic, and below diastolic pressures. Note in FIG. 6 that the upper microphone trace displays the pressure wave impinging against the upper edge of the cuff, and that evidence of this can be seen also in the lower trace, due to coupling of the wave front through the cuff. These signals are in phase as would be expected since there is negligible delay in coupling through the air chamber.

Figure 7:
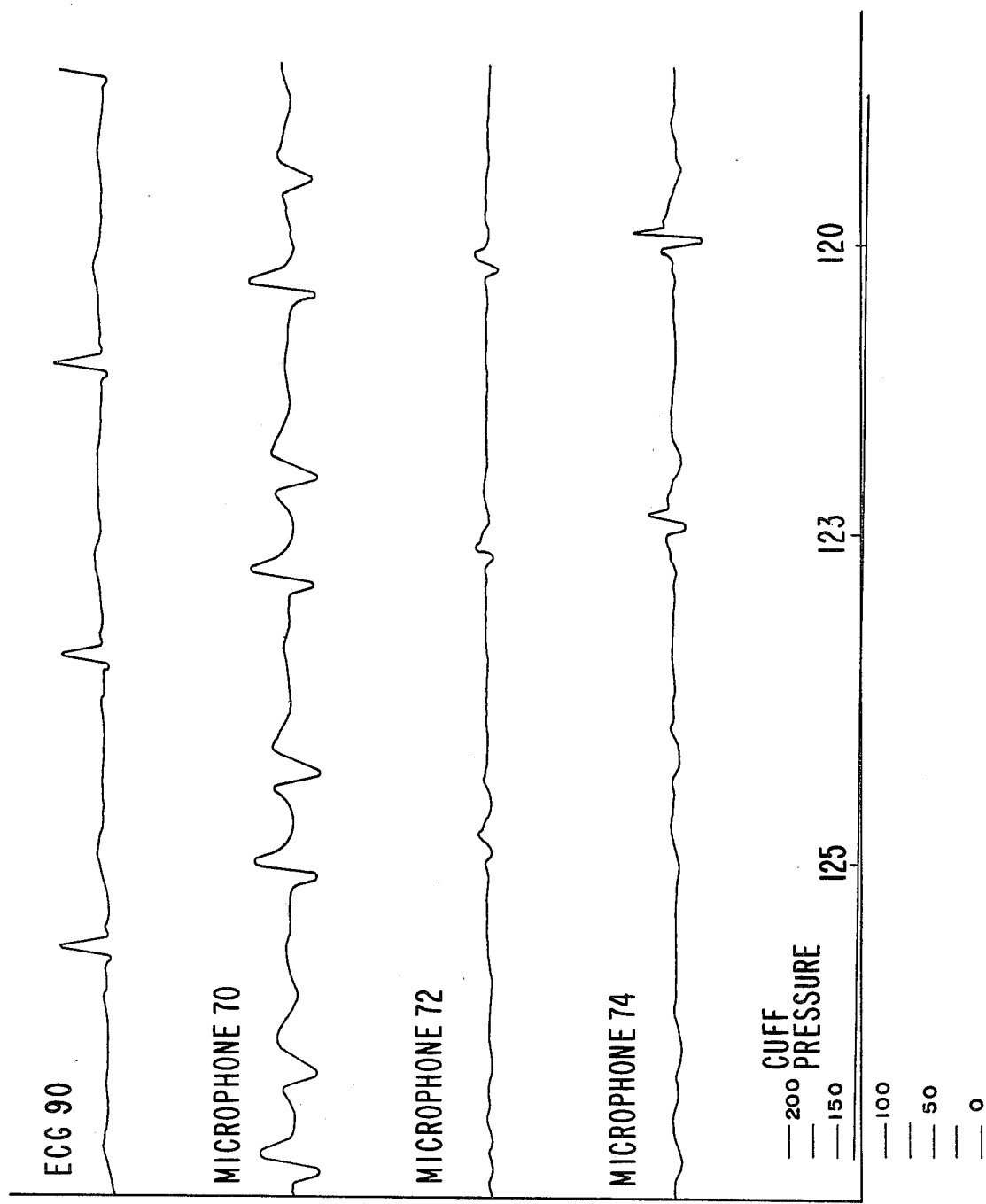

In FIG. 7, the first Korotkoff sound can be seen to occur in the lower microphone at a cuff pressure of 123 mm Hg, and the second at 120 mm Hg. The center microphone records the disturbance at 125 mm Hg when some flow actually approached that microphone, but insufficient flow took place to produce a sound at the lower microphone. This would suggest that in this instance the actual systolic pressure was slightly above 125 mm Hg.

Measurements of the time relationships of the events indicate a propagation velocity for the phenomenon of around 0.8 meter per second at this cuff pressure. This is probably explained by the fact that the artery is collapsed for the greater part of the cardiac cycle, and must be filled before the sounds can be produced at the middle and lower microphones.

Since the velocity of blood flow in this artery is around 0.7 meter per second, the time required for the blood to flow the 8 cm (estimated) from the upper edge of the occlusion to the lower microphone is around 100 milliseconds.

Figure 8:
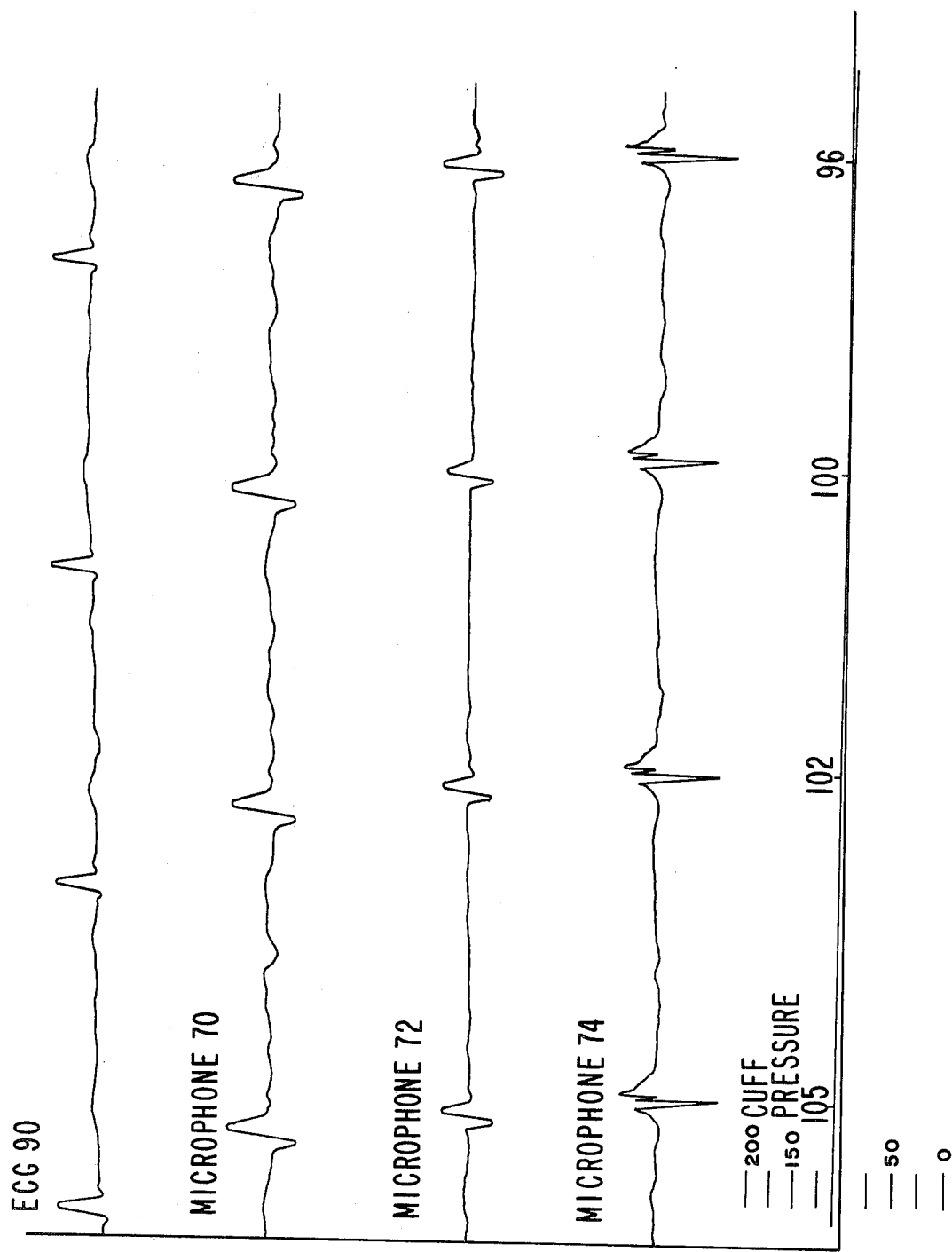

FIG. 8 shows the system with the cuff pressure in midrange between systolic and diastolic pressures. Signals in the upper and middle microphones are very similar, while the lower microphone exhibits a high amplitude, well developed Korotkoff sound. Time measurements assuming a propagation velocity here of 0.8 meter per second indicate that the artery is occluded to a point 6 cm above the lower microphone at the time of maximum occlusion.

Figure 9:
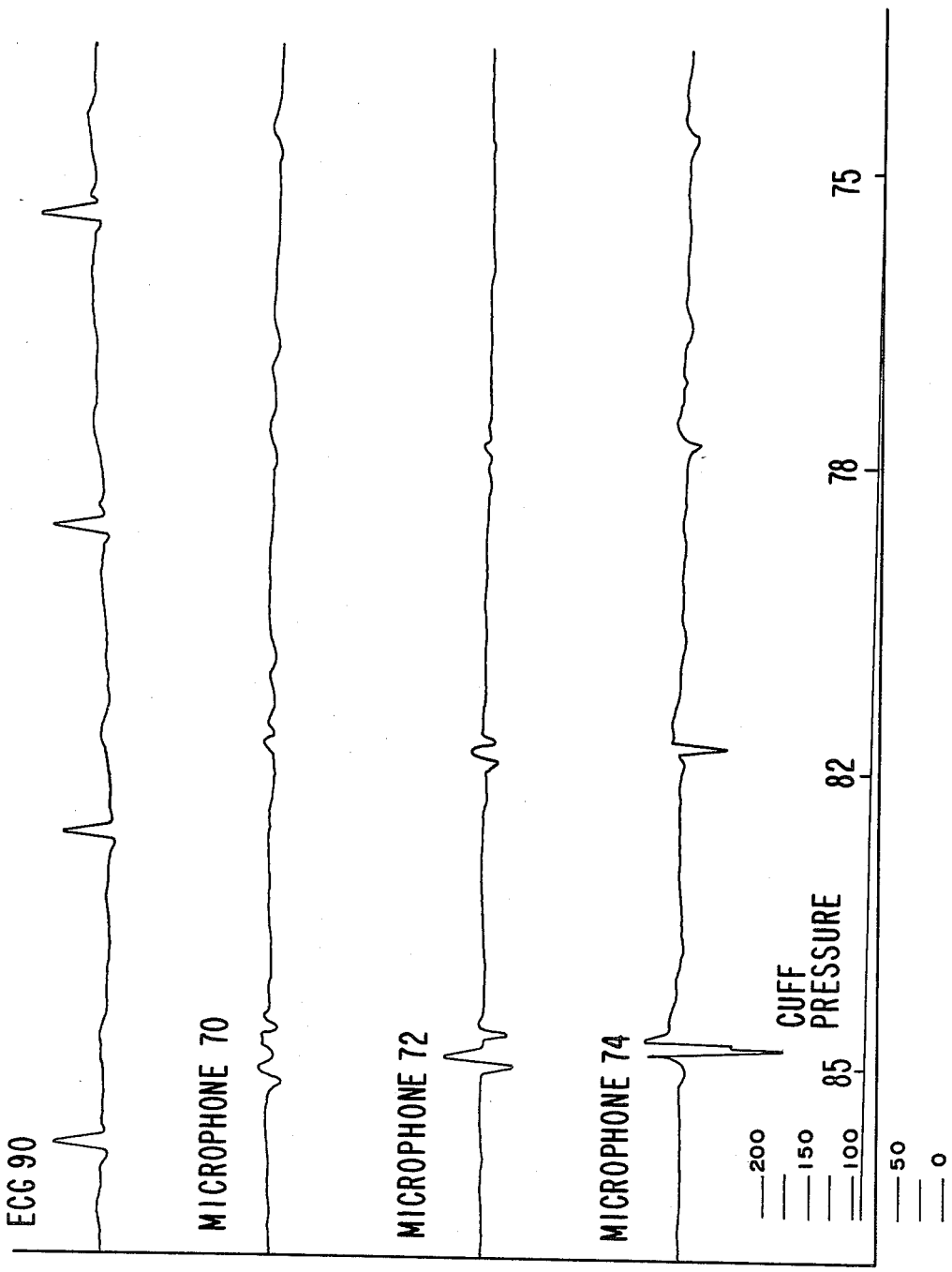
Figure 10:
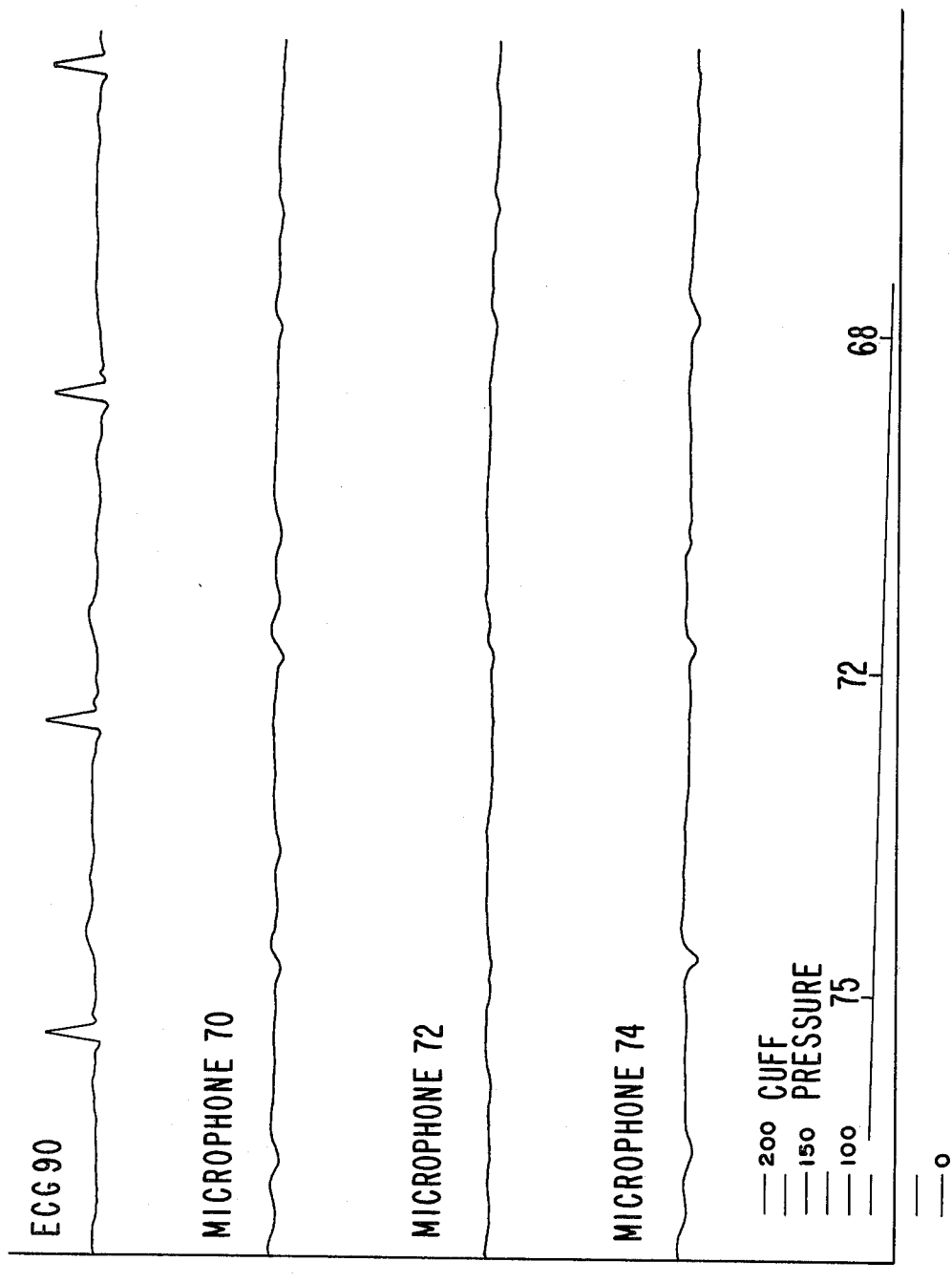

In FIG. 9, the final distinct Korotkoff sound can be seen in the lower microphone at a cuff pressure of 82 mm Hg, with propagation time of around 50 milliseconds, indicating an occluded length of 4 cm. The pulse at 78 mm Hg does show a trace of sudden wall motion associated with arterial collapse, and the actual diastolic pressure is probably between 75 and 78 mm Hg. FIG. 10 illustrates that, below diastolic pressure, the microphones all detect propagation of the arterial pressure wave down the brachial artery at a velocity of approximately 5 meters per second.

The patient from which the data of FIGS. 6–10 were obtained was a 60 year old male. Similar tests on a 28 year old male indicated a wave velocity of around 10 meters per second at cuff pressures below diastolic, with sound propagation velocities of 2.5 meters per second just above diastolic and 1 meter per second at systolic.

What is claimed is:

1. Apparatus for detecting Korotkoff sounds comprising: an inflatable cuff for surrounding an artery; a pair of microphones carried by the cuff at spaced locations thereon for sequentially sensing Korotkoff sounds when the cuff surrounds an artery; an electronic gate having a pair of inputs and an output; means including a signal delay unit for coupling one of the microphones to one of the inputs of the gate, the delay unit being operable to apply a signal to said one input of the gate to enable the gate after a first time interval following the sensing of a Korotkoff sound by the first microphone; and means coupled with the second microphone for connecting it to the second input of the gate to cause the gate to have an output signal when the signal from the second microphone occurs during a second time interval following the expiration of the first time interval.

2. Apparatus as set forth in claim 1, wherein said coupling means includes a multivibrator between the delay unit and the gate, said multivibrator being actuated after said first time interval to apply a control signal to said one input of the gate.

3. Apparatus as set forth in claim 1, wherein said coupling means includes an amplifier and a Schmitt trigger coupled in series between the first microphone and the delay unit.

4. Apparatus as set forth in claim 1, wherein said coupling means includes an amplifier and a Schmitt trigger in series between the first microphone and the delay unit, and a multivibrator between the delay unit and the gate, said multivibrator being actuated by said delay unit after said first time interval to apply a control signal to said one input of said gate.

5. An apparatus as set forth in claim 4, wherein the multivibrator is operable to apply said control signal to said one input of the gate during a time interval of approximately 80 milliseconds.

6. Apparatus as set forth in claim 1, wherein said connecting means includes a multivibrator capable of being actuated for a time interval of about 100 milliseconds.

7. Apparatus as set forth in claim 6, wherein is included an amplifier and a Schmitt trigger between the second microphone and the multivibrator.

8. Apparatus as set forth in claim 1, wherein the microphones are spaced a distance of about 5 centimeters apart.

9. A method of detecting Korotkoff sounds comprising: sensing a Korotkoff sound at one location on the brachial artery of a patient; enabling a gate following a time interval after the Korotkoff signal is sensed at said first location with the gate being capable of providing an output signal when an input signal is applied thereto and when the gate is enabled; sensing the same Korotkoff sound at a second location on the brachial artery after the time interval; generating an input signal as a function of the sensing of the Korotkoff sound at the second location; and applying the input signal to said gate while the gate is enabled to cause the gate to provide said output signal.

10. A method set forth in claim 9, wherein said enabling step includes enabling the gate for a time period greater than the time interval.

11. A method as set forth in claim 10, wherein said time interval is approximately 12 milliseconds and the time period is about 80 milliseconds.

12. A method as set forth in claim 9, wherein is included the step of providing a time delay between the time that the Korotkoff sound is sensed at the first location and the time that the gate is enabled, said time delay being for a time period substantially equal in length to said time interval.

13. A method as set forth in claim 9, wherein said enabling step includes generating a control signal for a second time interval after said first time interval, and applying the control signal to the gate to enable the same.

14. A method as set forth in claim 13, wherein the control signal is operable for a predetermined time period, said input signal being operable for a time span different in length from said time period.

15. A method as set forth in claim 14, wherein said time period is approximately 80 milliseconds and said time span is approximately 100 milliseconds.

* * * * *